United States Patent
Hedvati et al.

(10) Patent No.: US 7,678,938 B2
(45) Date of Patent: *Mar. 16, 2010

(54) OPTICAL RESOLUTION OF 3-CARBAMOYLMETHYL-5-METHYL HEXANOIC ACID

(75) Inventors: Lilach Hedvati, Doar Na Hefer (IL); Ziv Dee-Noor, Haifa (IL); Claude Singer, Kfar Saba (IL); Gideon Pilarski, Holon (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/893,235

(22) Filed: Aug. 14, 2007

(65) Prior Publication Data

US 2007/0287859 A1 Dec. 13, 2007

Related U.S. Application Data

(62) Division of application No. 11/432,010, filed on May 10, 2006.

(60) Provisional application No. 60/679,784, filed on May 10, 2005, provisional application No. 60/689,699, filed on Jun. 9, 2005, provisional application No. 60/733,009, filed on Nov. 2, 2005, provisional application No. 60/735,634, filed on Nov. 9, 2005, provisional application No. 60/740,950, filed on Nov. 29, 2005.

(51) Int. Cl.
C07B 57/00 (2006.01)
C07C 227/30 (2006.01)

(52) U.S. Cl. .................. 562/402; 562/401; 562/553; 562/554

(58) Field of Classification Search .................. None
See application file for complete search history.

(56) References Cited

U.S. PATENT DOCUMENTS

| | | | |
|---|---|---|---|
| 5,010,189 A * | 4/1991 | Herold et al. ............... 544/171 |
| 5,599,973 A | 2/1997 | Silverman et al. |
| 5,616,793 A | 4/1997 | Huckabee et al. |
| 5,629,447 A * | 5/1997 | Huckabee et al. ........... 562/553 |
| 5,637,737 A | 6/1997 | Andres et al. |
| 5,637,767 A | 6/1997 | Grote et al. |
| 6,001,876 A | 12/1999 | Singh |
| 6,187,930 B1 * | 2/2001 | Torrens-Jover et al. ... 548/375.1 |
| 6,197,819 B1 | 3/2001 | Silverman et al. |
| 6,333,198 B1 | 12/2001 | Edmeades et al. |
| 6,488,964 B2 | 12/2002 | Bruna et al. |
| 6,580,003 B2 | 6/2003 | Deng et al. |
| 6,642,398 B2 | 11/2003 | Belliotti et al. |
| 6,833,458 B2 | 12/2004 | Liu et al. |
| 6,891,059 B2 | 5/2005 | Burk et al. |
| 6,924,377 B2 | 8/2005 | Blazecka et al. |
| 7,141,695 B2 | 11/2006 | Przewosny et al. |
| 2001/0016665 A1 | 8/2001 | Grote et al. |
| 2003/0212290 A1 | 11/2003 | Burk et al. |
| 2003/0225149 A1 | 12/2003 | Blazecka et al. |
| 2005/0222464 A1 | 10/2005 | Hoge, II |
| 2005/0228190 A1 | 10/2005 | Bao et al. |
| 2005/0283023 A1 | 12/2005 | Hu et al. |
| 2006/0270871 A1 | 11/2006 | Khanduri et al. |
| 2007/0073085 A1 | 3/2007 | Hedvati et al. |
| 2007/0191636 A1 | 8/2007 | Kansal et al. |
| 2007/0197827 A1 | 8/2007 | Kansal et al. |
| 2008/0014280 A1 | 1/2008 | Kumar et al. |
| 2008/0311635 A1 | 12/2008 | Riva et al. |
| 2009/0143615 A1 | 6/2009 | Allegrini et al. |

FOREIGN PATENT DOCUMENTS

| | | |
|---|---|---|
| CN | 1 634 869 | 7/2005 |
| CZ | 297 970 | 3/2007 |
| WO | WO 96/38405 A1 | 12/1996 |
| WO | WO 96/40617 A1 | 12/1996 |
| WO | WO 01/55090 A1 | 8/2001 |
| WO | WO 2006/000904 A2 | 1/2005 |
| WO | WO 2005/100580 | 10/2005 |
| WO | WO 2006/008640 | 1/2006 |
| WO | WO 2006/110783 | 10/2006 |
| WO | WO 2006/121557 | 11/2006 |
| WO | WO 2006/122255 | 11/2006 |
| WO | WO 2006/122258 | 11/2006 |
| WO | WO 2006/136087 | 12/2006 |
| WO | WO 2007/035789 | 3/2007 |
| WO | WO 2007/035890 | 3/2007 |
| WO | WO 2008/004044 | 1/2008 |
| WO | WO 2008/007145 | 1/2008 |
| WO | WO 2008/009897 | 1/2008 |
| WO | WO 2008/040935 | 4/2008 |
| WO | WO 2008/062460 | 5/2008 |
| WO | WO 2009/010554 | 11/2009 |

OTHER PUBLICATIONS

Hoekstra et al. "Chemical Development of CI-1008, An Enantiomerically Pure Anticonvulsant", Organic Process Research and Development, vol. 1, No. 1, pp. 26-38, (1997).

Martin et al. "Pregabalin: CI-1008, PD-144723" Drugs of the Future, vol. 24, No. 8, pp. 862-870, (1999).

(Continued)

*Primary Examiner*—Daniel M Sullivan
*Assistant Examiner*—Yevegeny Valenrod
(74) *Attorney, Agent, or Firm*—Kenyon & Kenyon LLP

(57) ABSTRACT

The invention relates to pure (R)-CMH and to the optical resolution of CMH-racemate, a key intermediate in the synthesis of (S)-Pregabalin. The invention also relates to the process for optically purifying (R)-CMH and to the process for isolating (S)-CMH from the mother liquor.

45 Claims, No Drawings

OTHER PUBLICATIONS

Andruszkiewicz and Silverman, "A Convenient Synthesis of 3-Alkyl-4-Aminobutanoic Acids," *Synthesis*, 953-955 (1989).

Barnes, D.M., et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram," *J. Am. Chem. Soc.*, 124(44): 13097-13105 (2002).

Berner et al. "Asymmetric Michael Additions to Nitroalkenes," *European Journal of Organic Chemistry*, 1877-1894 (2002).

Cason, J. et al., "Branched-Chain Fatty Acids. XXVII. Further Study of the Dependence of Rate of Amide Hydrolysis on Substitution near the Amide Group. Relative Rates of Hydrolysis of Nitrile to Amide and Amide to Acid," *J. Org. Chem.*, 18(9): 1129-1136 (1953).

Chen, Ao et al., "Synthesis of Pregabalin," *Zhongguo YiYao Gongye Zazhi*, 35(4): 195-196 (2004).

Colonge et al., "Preparation De Pyrrolidones-2 et de Gamma-Aminoacides," *Bulletin De La Societe Chimique De France, Societe Francaise De Chimie*, 598-603 (1962).

Day and Thorpe, "The Formation and Reactions of Imino-compounds. Part XX. The Condensation of Aldehydes with Cyanoacetamide," *J. Chem. Soc.*, 117: 1465-1474 (1920).

Karanewsky, D.S. et al., "Practical Synthesis of an Enantiomerically Pure Synthon for the Preparation of Mevinic Acid Analogues," *J. Org. Chem.*, 56(11): 3744-3747 (1991).

Li, H. et al., "Highly Enantioselective Catalytic Conjugate Addition of Malonate and β-Ketoester to Nitroalkenes: Asymmetric C-C Bond Formation with New Bifunctional Organic Catalysts Based on Cinchona Alkaloids," *J. Am. Chem. Soc.*, 126(32): 9906-9907 (2004).

Okino, T. et al., "Enantio- and Diastereoselective Michael Reaction of 1,3-Dicarbonyl Compounds to Nitroolefins Catalyzed by a Bifunctional Thiourea," *J. Am. Chem. Soc.*, 127(1): 119-125 (2005).

Sammis, G.M. et al., "Highly Enantioselective Catalytic Conjugate Addition of Cyanide to α,β-Unsaturated Imides", *J. Am. Chem. Soc.*, 125(15): 4442-43 (2003).

Shintani et al., "Highly Enantioselective Desymmetrization of Anhydrides by Carbon Nucleophiles: Reactions of Grignard Reagents in the Presence of(-)-Sparteine," *Angewandte Chemie, International Edition*, 41(6): 1057-1059 (2002).

Snyder et al., Introduction to Modern Liquid Chromatography, 549-572 (2d ed., John Wiley & Sons, 1979).

Strobel et al., Chemical Instrumentation: A Systematic Approach, 391-393, 879-894, 922-925, 953 (3d ed. 1989).

Theisen, P.D. et al., "Prochiral Recognition in the Reaction of 3-Substituted Glutaric Anhydrides with Chiral Secondary Alcohols," *J. Org. Chem.*, 58(1): 142-146 (1993).

Verma, Rekha et al., "Desymmetrization of prochiral anhydrides with Evans' oxazolidinones: an efficient route to homochiral glutaric and adipic acid derivatives," *J. Chem. Soc., Perkin Transactions 1: Organic and Bio-Organic Chemistry*, 257-264 (1999).

Yamamoto et al., "Stereoselective Synthesis of (E)-Alkylidenesuccinates by Palladium-catalyzed Carbonylation," *Bull. Chem. Soc. Japan*, 58(11): 3397-3398 (1985).

Burk et al., "An Enantioselective Synthesis of (S)-(+)-3-Aminomethyl-5-methylhexanoic Acid via Asymmetric Hydrogenation," *J. Org. Chem.*, 68: 5731-5734 (2003).

Hiratake et al., "Enantiotopic-group Differentiation. Catalytic Asymmetric Ring-opening of Prochiral Cyclic Acid Anhydrides with Methanol, using Cinchona Alkaloids," *J. Chem. Soc., Perkin Trans. 1*, Issue 1: 1053-1058 (1987).

Lin et al., "Chiral HPLC Separations for Process Development of S-(+)-Isobutyl GABA, A Potential Anti-Epileptic Agent," *J. Liq. Chrom.*, 19(16):2699-2708 (1996).

Serfass et al., "General Synthesis of 3-Substituted Alkenyl GABA as Potential Anticonvulsants," *Biorganic & Medicinal Chemistry Letters*, 8: 2599-2602 (1998).

Yuen et al., "Enantioselective Synthesis of PD144723: A Potent Stereospecific Anticonvulsant," *Biorganic & Medicinal Chemistry Letters*, 4(6): 823-826 (1994).

\* cited by examiner

OPTICAL RESOLUTION OF 3-CARBAMOYLMETHYL-5-METHYL HEXANOIC ACID

RELATED APPLICATIONS

This application is a divisional of U.S. patent application Ser. No. 11/432,010, filed May 10, 2006, which claims the benefit of priority to U.S. provisional application Nos. 60/679,784, filed May 10, 2005, 60/689,699, filed Jun. 9, 2005, 60/733,009, filed Nov. 2, 2005, 60/735,634, filed Nov. 9, 2005, and 60/740,950, filed Nov. 29, 2005, the contents of which are incorporated herein by reference in their entirety.

FIELD OF THE INVENTION

The present invention is directed to pure (R)-CMH, the optical resolution of 3-carbamoylmethyl-5-methyl hexanoic acid-racemate (CMH-racemate), the process for optically purifying (R)-CMH and the process for isolating (S)-CMH from the mother liquor.

BACKGROUND OF THE INVENTION (S)-Pregabalin, (S)-(+)-3-(aminomethyl)-5-methylhexanoic acid, a compound having the chemical structure,

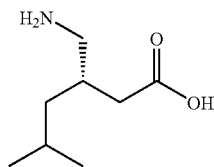

is also known as γ-amino butyric acid or (S)-3-isobutyl GABA. (S)-Pregabalin has been found to activate GAD (L-glutamic acid decarboxylase). (S)-Pregabalin has a dose dependent protective effect on-seizure, and is a CNS-active compound. (S)-Pregabalin is useful in anticonvulsant therapy, due to its activation of GAD, promoting the production of GABA, one of the brain's major inhibitory neurotransmitters, which is released at 30 percent of the brains synapses. (S)-Pregabalin has analgesic, anticonvulsant, and anxiolytic activity.

In the synthesis disclosed in U.S. Pat. No. 5,616,793, (S)-Pregabalin is obtained after optical resolution of the (±)-3-(carbamoylmethyl)-5-methylhexanoic acid racemate (referred to as CMH-racemate), which is accomplished by reaction of the CMH-racemate with chiral phenylethylamine in a solvent mixture of $CHCl_3$ and ethanol to obtain the desired R-enantiomer of CMH according to the following scheme:

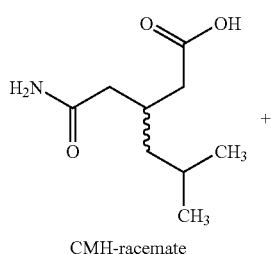

CMH-racemate

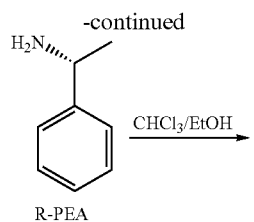

R-PEA

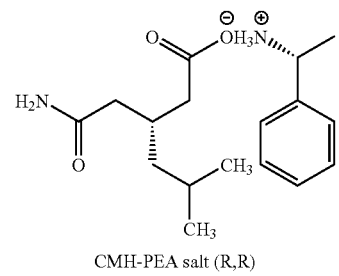

CMH-PEA salt (R,R)

However, according to *Chemical Development of CI*-1008, *An Enantiomerically Pure Anticonvulsant*, ORGANIC PROCESS RESEARCH & DEVELOPMENT, 1997, 1, 26-38, this synthetic method was avoided because it requires the use of chloroform.

In the synthesis disclosed in DRUGS OF THE FUTURE, 24 (8), 862-870 (1999), CMH-racemate is also resolved with (R)-1-phenylethylamine, yielding the (R)-phenylethylamine salt of (R)-CMH. Combining the salt with an acid liberates the R enantiomer. Finally, Hoffmann degradation with $Br_2$/NaOH provides (S)-Pregabalin. However, the optical resolution is done using a mixture of EtOH and chloroform, and therefore is problematic.

Optical resolution of a racemic mixture, particularly of carboxylic acids and amines, is performed via a diastereomeric salt. An example of this method is depicted in the following scheme,

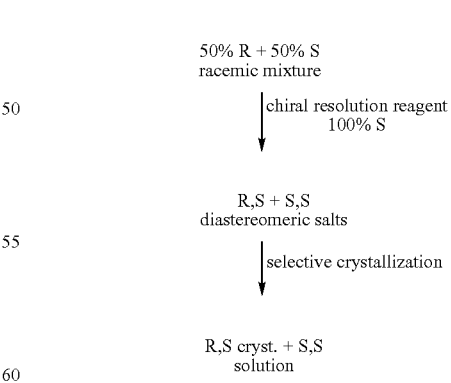

The salt is formed by reacting the racemic mixture with a chiral resolving reagent. Then, a selective crystallization of only one of the diastereomers is done to isolate the desired diastereomer salt, while the undesired remains in the solution.

The crystalline salt is then isolated and the chiral resolving reagent is removed to give the desired enantiomer. Accordingly, CMH which has a carboxylic acid function can be reacted with an appropriate chiral amine to obtain the salt of the desirable enantiomer (R-enantiomer), which is then isolated followed by removing the chiral amine to give (R)-CMH.

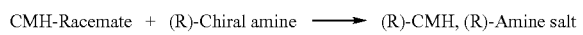

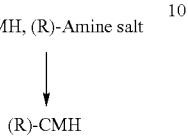

Thus, there is a need for an optical resolution process that overcomes the limitations of the above resolution procedures.

SUMMARY OF THE INVENTION

In one embodiment, the present invention provides (R)-CMH containing less than about 0.2% area by HPLC of (S)-CMH. Preferably, the present invention provides (R)-CMH containing less than about 0.1% area by HPLC of (S)-CMH.

In another embodiment, the present invention provides a process for the optical resolution of (±)-3-(carbamoylmethyl)-5-methylhexanoic acid (referred to as CMH-racemate),

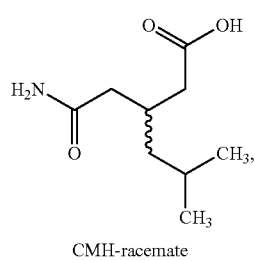

CMH-racemate comprising combining CMH-racemate, a solvent selected from the group consisting of ketone, ester, nitrile, $C_{1-4}$ alcohol, water, or mixtures thereof, a chiral resolving reagent of amino alcohol and salts thereof; recovering; and adding a solvent selected from the group consisting of ketone, $C_{1-8}$ alcohol, water or mixtures thereof, and a strong mineral acid, wherein; any individual stereoisomer of the chiral resolving reagent may be used.

In yet another embodiment the present invention also provides a process for the optical resolution CMH-racemate that comprises two steps: the first is the preparation of the (R)-CMH amine salt and the second, recovering (R)-CMH from the salt. The process comprises combining CMH-racemate, a solvent selected from the group consisting of ketone, ester, nitrile, $C_{1-4}$ alcohol, water, or mixtures thereof, a chiral resolving reagent selected from ephedrine, ephedrine salt, norephedrine, and norephedrine salt to obtain a precipitate, wherein the precipitate is of (R)-CMH-ephedrine salt of the following structure:

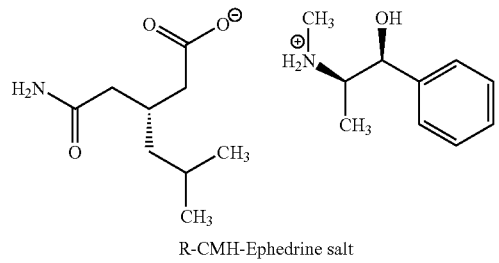

R-CMH-Ephedrine salt or of (R)-CMH-norephedrine salt of the following structure:

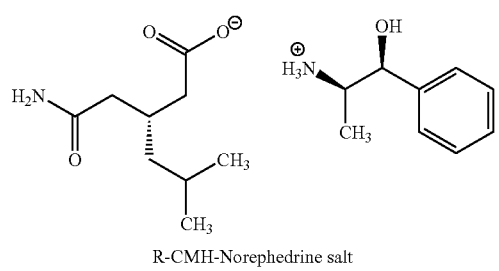

R-CMH-Norephedrine salt

The precipitate is further isolated and thereafter combined with a solvent selected from the group consisting of ketone, $C_{1-8}$ alcohol, water, or mixtures thereof, and with a strong mineral acid to obtain a precipitate of (R)-CMH of the following structure

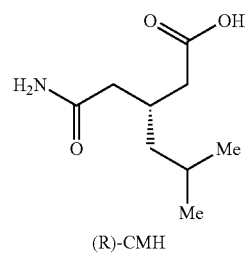

(R)-CMH

In one embodiment the present invention provides a process for the optical resolution of (±)-3-(carbamoylmethyl)-5-methylhexanoic acid (referred to as CMH-racemate) comprising combining CMH-racemate, a solvent selected from ketone, ester, nitrile, $C_{1-4}$ alcohol, water, or mixtures thereof, and 1R, 2S-(−)-ephedrine to obtain a reaction mixture. The obtained reaction mixture is then heated to a temperature of about 50° C. to about 140° C. The reaction mixture is then cooled to a temperature of about ambient to about 2° C. to obtain a precipitate, wherein the precipitate is of (R)-CMH-ephedrine salt of the following structure:

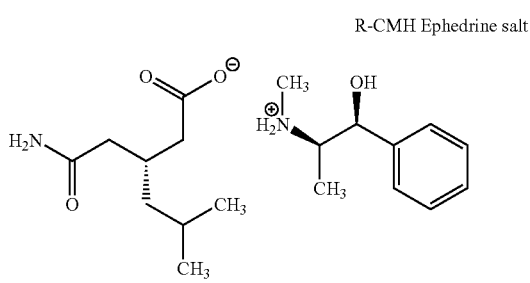

R-CMH Ephedrine salt

The precipitate is further isolated and thereafter combined with a solvent selected from the group consisting of ketone, $C_{1-8}$ alcohol, water or mixtures thereof, and with a strong mineral acid to obtain a slurry and the slurry is then cooled to a temperature of about 10° C. to about 2° C. to obtain a precipitate of (R)-CMH of the following structure

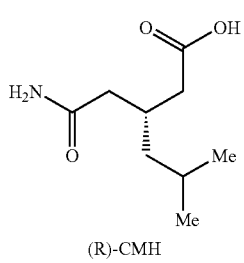

(R)-CMH

In another embodiment, the present invention provides (R)-CMH-Ephedrine salt.

In yet another embodiment, the present invention provides a process for improving the optical purity of (R)-CMH comprising combining (R)-CMH with water.

In one embodiment, the present invention provides a process for isolating (S)-CMH from the remaining mother liquor comprising combining the mother liquor obtained after the filtration of (R)-CMH with water, and heating to dissolution. The solution is then cooled and combined with an acid to obtain a precipitate of CMH containing about a specific amount of (S)-CMH. The precipitate is then filtered and resolved again with acetone, and ephedrine as a chiral resolving reagent to obtain a second precipitate of R-CMH-ephedrine salt that is then removed. The remaining mother liquor, which contains (S)-CMH-ephedrine salt, is then evaporated to dryness, and the residue is treated with an acid to obtain (S)-CMH, which is further recovered In another embodiment, the present invention provides a process for preparing (S)-Pregabalin comprising preparing (R)-CMH by the process of the present invention, and converting it to (S)-Pregabalin.

DETAILED DESCRIPTION OF THE INVENTION

As used herein, the term "chiral resolving reagent" refers to an acidic or basic structure that can lead to the precipitation of the diastereomer containing the desired enantiomer in high chemical and optical yields.

As used herein, the term "racemate" refers to a mixture that contains an equal amount of enantiomers.

The present invention provides (R)-CMH containing less than about 0.2% area by HPLC of (S)-CMH. Preferably, the present invention provides (R)-CMH containing less than about 0.1% area by HPLC of (S)-CMH.

The process of the present invention performs resolution at the stage of CMH-racemate, of the following structure

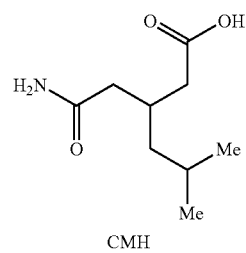

CMH without using carcinogenic solvents as chloroform, while also recycling the undesired enantiomer. However, some processes of the prior art perform the optical resolution on Pregabalin itself while, recycling (R)-Pregabalin is very difficult, thus leading to a non-efficient and non-economical process.

The present invention provides a process for the optical resolution of (±)-3-(carbamoylmethyl)-5-methylhexanoic acid (referred to as CMH-racemate),

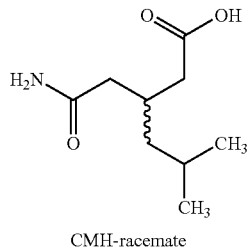

CMH-racemate comprising combining CMH-racemate, a solvent selected from the group consisting of ketone, ester, nitrile, $C_{1-4}$ alcohol, water, or mixtures thereof, a chiral resolving reagent of amino alcohol and salts thereof to obtain a precipitate; isolating the precipitate; and adding a solvent selected from the group consisting of ketone, $C_{1-8}$ alcohol, water or mixtures thereof, and a strong mineral acid, wherein; any individual stereoisomer of the chiral resolving reagent may be used.

The present invention also provides a process for the optical resolution CMH-racemate that comprises two steps: the first is the preparation of the (R)-CMH amine salt and the second, recovering (R)-CMH from the salt. The process comprises combining CMH-racemate, a solvent selected from the group consisting of ketone, ester, nitrile, $C_{1-4}$ alcohol, water, or mixtures thereof, a chiral resolving reagent selected from ephedrine, ephedrine salt, norephedrine, and norephedrine salt to obtain a precipitate, wherein the precipitate is of (R)-CMH-ephedrine salt of the following structure:

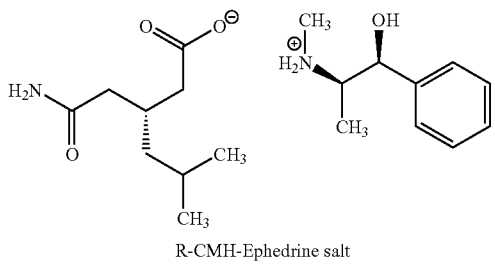

R-CMH-Ephedrine salt or of (R)-CMH-norephedrine salt of the following structure:

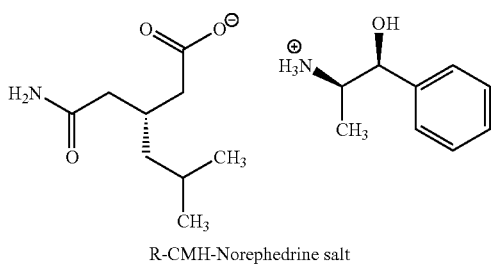

R-CMH-Norephedrine salt

The precipitate is further isolated and thereafter combined with a solvent selected from the group consisting of ketone, $C_{1-8}$ alcohol, water, or mixtures thereof, and with a strong mineral acid to obtain a precipitate of (R)-CMH of the following structure

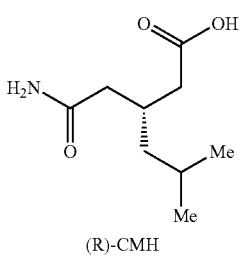

(R)-CMH

The present invention provides a process for the optical resolution of CMH-racemate comprising combining CMH-racemate, a solvent selected from ketone, ester, nitrile, $C_{1-4}$ alcohol, water, or mixtures thereof, and 1R, 2S-(−)-ephedrine to obtain a reaction mixture. The obtained reaction mixture is then heated to a temperature of about 50° C. to about 140° C. The reaction mixture is then cooled to a temperature of about 20° C. to about −20° C. to obtain a precipitate, wherein the precipitate is of (R)-CMH-ephedrine salt of the following structure:

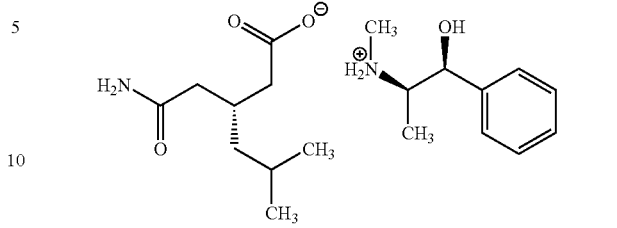

R-CMH Ephedrine salt

The precipitate is further isolated and thereafter combined with a solvent selected from the group consisting of ketone, $C_{1-8}$ alcohol, water or mixtures thereof, and with a strong mineral acid to obtain a slurry and the slurry is then cooled to a temperature of about 10° C. to about 2° C. to obtain a precipitate of (R)-CMH of the following structure

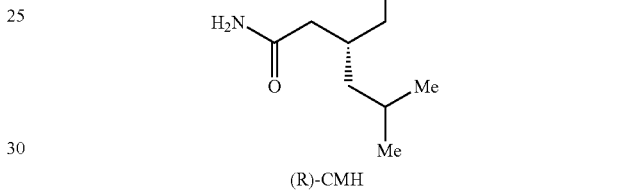

(R)-CMH

Preferably, the chiral resolving reagent of amino alcohol and salts thereof is selected from the group consisting of ephedrine, ephedrine salt, norephedrine, and norephedrine salt. More preferably, the chiral resolving reagent is ephedrine or ephedrine salt. Most preferably, the chiral resolving reagent is 1R,2S-(−)-ephedrine.

Preferably, the salt of ephedrine or norephedrine is a hydrochloride, nitrate, or sulfate. More preferably, the salt is a hydrochloride.

Optionally, a base is further added with the resolving reagent. When the chiral resolving reagent is the salt of ephedrine or of norephedrine, a base must also be used. Preferably, the base is either an organic base or an inorganic base. Preferably, the organic base is an amine. Preferably, the amine is tertiary or secondary amine. Preferably, the tertiary amine is triethylamine or tributylamine. Preferably, the secondary amine is diisopropylamine or di-n-propyl amine. The more preferred organic base is triethylamine. Preferably, the inorganic base is alkali metal hydrogen carbonates, alkali hydroxide or alkali carbonate. Preferably, the alkali hydroxide is either NaOH or KOH. Preferably, the alkali carbonate is either $K_2CO_3$ or $Na_2CO_3$. The more preferred inorganic base is NaOH.

Preferably, the ketone is a $C_2$ to $C_6$ ketone, more preferably a $C_2$ to $C_5$ ketone, more preferably, acetone or methylisobutyl ketone, most preferably, acetone. Preferably, the $C_{1-4}$ alcohol is selected from the group consisting of methanol, ethanol, isopropanol, or isobutanol. More preferably, the $C_{1-4}$ alcohol is methanol. Preferably, the ester is selected from a $C_3$ to $C_8$, more preferably a $C_4$ to $C_6$ ester, such as a $C_2$ to $C_4$ alkylacetate. More preferably, the ester is selected from the group consisting of ethyl acetate, butylacetate and isopropyl acetate. Most preferably, the ester is Ethylacetate. Preferably, the nitrile is acetonitrile. The most preferred solvent is acetone or a mixture of acetone and water.

Preferably, the mixture is heated to a temperature of about 50° C. to about 100° C. obtain a reaction mixture, which is maintained at this temperature for about 0.5 hour to about 5 hours, more preferably, for about 0.5 hour to about 2 hours. Preferably, the reaction mixture is a solution.

The obtained reaction mixture is cooled to a temperature of about 20° C. to about −20° C., and is preferably maintained for about an hour to about 24 hours, more preferably, for an hour to about 12 hours.

Preferably, the isolation is by recovering.

Preferably, the strong mineral acid is HCl, HBr, $H_2SO_4$, or $H_2PO_3$. The more preferred strong mineral acid is HCl.

Preferably, after the addition of the acid, a pH of about 0 to about 4 is obtained, more preferably, a pH of about 1 to about 3 is obtained.

Preferably, the slurry is cooled to a temperature of about 2° C.

Preferably, the slurry is maintained at a temperature of about 2° C. to about ambient temperature, more preferably, of about 2° C. to about 10° C., for about 0.5 hours to about 24 hours, more preferably, for about 0.5 hours to about 2 hours.

Preferably, the (R)-CMH is further recovered.

(R)-CMH, (R)-CMH-ephedrine salt and (R)-CMH-norephedrine salt may be recovered by known methods in the art, such as filtering, washing, and drying in a vacuum oven. After the filtration step, the remaining mother liquor is obtained.

The (R)-CMH obtained by the process of the invention contains less than about 7% area by HPLC, more preferably, less than about 4% area by HPLC, most preferably, less than about 0.2% area by HPLC and even most preferably, less than 0.1% area by HPLC of (S)-CMH.

The present invention provides (R)-CMH-Ephedrine salt.

The present invention provides a process for optically purifying (R)-CMH comprising combining (R)-CMH with water. Preferably, the water is in an amount of 8-15 vol.

Preferably, the (R)-CMH has a specific optical purity as measured by HPLC. The combination of (R)-CMH and water results in a slurry. Preferably, the obtained slurry is stirred to obtain a precipitate of (R)-CMH. Preferably, the obtained slurry is stirred at a temperature of about 2° C. to about 30° C. for about one hour to about 24 hours, more preferably, at a temperature of about 15° C. to about 20° C. for about 0.5 hour to about 24 hours, most preferably, at a temperature of about 20° C. for about one hour to about 2 hours.

The starting (R)-CMH may be obtained by the processes described before, having a purity of about 90% to about 99% area by HPLC, more preferably, of about 96.5% to about 99% area by HPLC.

(R)-CMH obtained by the above process contains less than about 1% area by HPLC, more preferably, less than about 0.2% area by HPLC, most preferably, less than 0.1% area by HPLC of (S)-CMH.

Preferably, the precipitate is recovered. The precipitate may be recovered by any method known in the art, such as filtering, washing, and drying.

The present invention provides a process for isolating (S)-CMH from the remaining mother liquor comprising combining the mother liquor obtained after the flirtation of (R)-CMH with water, and heating to dissolution. The solution is then cooled and combined with an acid to obtain a precipitate of CMH containing about a specific amount of (S)-CMH. The precipitate is then filtered and resolved again with acetone, and 1R, 2S-(−)-ephedrine to obtain a second precipitate of R-CMH-ephedrine salt that is then removed. The remaining mother liquor, which contains (S)-CMH-ephedrine salt, is then evaporated to dryness, and the residue is treated with an acid to obtain (S)-CMH, which is further recovered.

Preferably, when the precipitate is resolved again with acetone and ephedrine a base is also added.

The precipitate of (S)-CMH may be recovered by known methods in the art, such as filtering, washing and drying in a vacuum oven.

The present invention provides a process for preparing (S)-Pregabalin comprising preparing (R)-CMH by the process of the present invention, and converting it to (S)-Pregabalin. Preferably, the conversion of (R)-CMH to (S)-Pregabalin comprises reacting (R)-CMH with bromine in a Hoffman reaction under basic conditions at a temperature of about 60° C. to about 85° C., to obtain a basic mixture, followed by an addition of a strong mineral acid, to obtain an acidic mixture containing a complex of (S)-Pregabalin with the strong mineral acid, as disclosed in Co-application No. 60/689,699, or by any other process known to one skilled in the art.

Preferably, the (S)-Pregabalin contains less than about 0.2% area by HPLC of (R)-Pregabalin. More preferably, (S)-Pregabalin contains less than about 0.1% area by HPLC of (R)-Pregabalin.

The present invention provides a pharmaceutical composition comprising (S)-Pregabalin made by the process of the present invention and at least one pharmaceutically acceptable excipient.

The present invention provides a process for preparing a pharmaceutical formulation comprising combining (S)-Pregabalin made by the process of the present invention, with at least one pharmaceutically acceptable excipient.

The present invention provides the use of (S)-Pregabalin made by the process of the present invention for the manufacture of a pharmaceutical composition.

Methods of administration of a pharmaceutical composition of the present invention can be administered in various preparations depending on the age, sex, and symptoms of the patient. The pharmaceutical compositions can be administered, for example, as tablets, pills, powders, liquids, suspensions, emulsions, granules, capsules, suppositories, injection preparations (solutions and suspensions), and the like.

Pharmaceutical compositions of the present invention can optionally be mixed with (S)-Pregabalin obtained in the present invention and other active ingredients. In addition, pharmaceutical compositions of the present invention can contain inactive ingredients such as diluents, carriers, fillers, bulking agents, binders, disintegrants, disintegration inhibitors, absorption accelerators, wetting agents, lubricants, glidants, surface active agents, flavoring agents, and the like.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. EUDRAGIT®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. AC-DI-SOL®, PRIMELLOSE®), colloidal silicon dioxide, croscarmellose sodium, crospovidone (e.g. KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g. EXPLOTAB®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, the (S)-Pregabalin and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxy toluene, butylated hydroxyanisole, and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

When preparing injectable (parenteral) pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic. Additional ingredients, such as dissolving agents, buffer agents, and analgesic agents may be added.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages can be conveniently presented in unit dosage form and prepared by any of the methods well-known in the pharmaceutical arts.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

Instruments

HPLC

| Enantiomeric purity of R-3-(Carbamoylmethyl)-5-methylhexanoic acid (CMH) by chiral HPLC | |
|---|---|
| HPLC | |
| Column & packing | DAICEL Chiralpak AD-H 250*4.6 mm 5 μm P.N. 19325 |
| Eluent: | n-Heptane:Ethanol:TFA 850:150:1 TFA from J. T. Baker 9470-01 recommended |
| Stop time: | 25 min |
| Flow: | 0.5 ml/min |
| Detector: | 208 nm. |
| Injection volume: | 50 μl. |
| Diluent | 85:15 n-Heptane:Ethanol |
| Column temperature | 10° C. |
| Autosampler temperature | 15° C. |

Typical Relative Retention Times are:

R-CMH-R-(+)-3-(Carbamoylmethyl)-5-methylhexanoic acid RRT=1.00

S-CMH-S-(−)-3-(Carbamoylmethyl)-5-methylhexanoic acid RRT=1.14

EXAMPLES

Example 1

Optical Resolution of (R)-CMH-Ephedrine Salt

A 250 ml flask was charged with 100 ml of acetone, 10 ml of methanol, 10 g of CMH-racemate, and 4.4 g of 1R, 2S-(−)-ephedrine. The resulting clear solution was evaporated to dryness, and 100 ml of acetone was added to the residue. After stirring for 1 hour at room temperature, the precipitate was filtered, washed with 40 ml of acetone, and dried at 45° C. at a pressure of 10 mm Hg. The (R)-CMH-ephedrine salt was found to have an optical purity of 99.3% area by HPLC.

Example 2

Optical Resolution of (R)-CMH-Ephedrine Salt

A 100 ml flask was charged with 40 ml of acetone, 5 g of CMH-racemate, and 4.4 g of 1R, 2S-(−)-ephedrine. The mixture was heated to dissolution, and then cooled to 10° C. After stirring for 1 hour at 10° C., the resulting precipitate was filtered, washed with 10 ml of acetone, and dried at 45° C. at a pressure of 10 mm Hg. The (R)-CMH-ephedrine salt was found to have an optical purity of 97% area by HPLC.

Example 3

Optical Resolution of (R)-CMH-Ephedrine Salt

A 100 ml flask was charged with acetone (80 ml), CMH-racemate (10 gr), Triethylamine (5.4 gr) and 1R, 2S-(−)-Ephedrine hydrochloride (10.79 gr). The mixture was heated to reflux and stirred at reflux for 2 h. The mixture was cooled to 10° C., and after stirring for 1 h at 10° C. the precipitate was filtered, washed with acetone (10 ml) and dried at 45° C. under 10 mm Hg. (R)-CMH-ephedrine salt was obtained (9.95 gr), 90.2% optical pure.

Example 4

Preparation of (R)-CMH from (R)-CMH-Ephedrine Salt

A 100 ml flask was charged with water (22 ml), HCl-32% (2 ml) and CMH-ephedrine salt (GP-4328, 6 gr). The mixture was stirred at room temperature for 15 min, then was cooled to 2° C., and stirred for 2 h. The precipitate was filtered, washed with water (5 ml) and dried at 45° C. under 10 mm Hg. (R)-CMH was obtained (1 gr), 93.6% optical pure.

Example 5

Optical Resolution of (R)-CMH-Ephedrine Salt

A 100 ml flask was charged with acetone (80 ml), CMH-racemate (10 gr), NaOH (2.14 gr) and 1R, 2S-(−)-Ephedrine hydrochloride (10.79 gr). The mixture was heated to reflux and stirred at reflux for 2 h. The mixture was cooled to 10° C., and after stirring (1 h) at 10° C. the precipitate was filtered, washed with acetone (10 ml) and dried at 45° C. under 10 mm Hg. (R)-CMH-ephedrine salt was obtained (9.65 gr), 94.6% optical pure.

Example 6

Preparation of (R)-CMH from (R)-CMH-Ephedrine Salt

A 100 ml flask was charged with water (22 ml), HCl-32% (2 ml) and (R)-CMH-ephedrine salt (6 gr, optical purity of 94.6%).). The mixture was stirred at RT for 15 min, then was cooled to 2° C., and stirred for 2 h. The precipitate was filtered, washed with water (5 ml) and dried at 45° C. under 10 mm Hg. (R)-CMH was obtained (2.1 gr), 98.5% optical pure.

Example 7

Optical Resolution of (R)-CMH-Ephedrine Salt

A 1 L flask was charged with acetone (480 ml), CMH-racemate (60 gr), NaOH (12.84 gr) and 1R, 2S-(-)-Ephedrine hydrochloride (64.74 gr). The mixture was heated to reflux and stirred at reflux for 2 h. The mixture was cooled to 10° C., and after stirring (1 h) at 10° C. the precipitate was filtered, washed with acetone (60 ml) and dried at 45° C. under 10 mm Hg. (R)-CMH-ephedrine salt was obtained (56 gr), 98.8% optical pure.

Example 8

Preparation of (R)-CMH from (R)-CMH-Ephedrine Salt

A 0.5 L flask was charged with water (216 ml), and (R)-CMH-ephedrine salt (54 gr, optical purity of 99.7%). The mixture was stirred at RT until dissolution, and HCl-32% (15 ml) was added to obtain pH=1. The solution was cooled to 2° C., stirred for 1 h, after which the precipitate was filtered, washed with water (54 ml) and dried at 45° C. under 10 mm Hg. (R)-CMH was obtained (20 gr), 99.7% optical pure.

Example 9

Slurry of (R)-CMH in Water (Improve Optical Purity)

A mixture of (R)-CMH (40 gr, 96.5% optical pure) in water (400 ml) was stirred for 1 h at RT. The solid was filtered, washed with water (80 ml) and dried at 45° C. under 10 mm Hg. (R)-CMH was obtained (34.5 gr), 99.7% optical pure.

Example 10

Preparation of (R)-CMH (All Steps)

A 1 L flask was charged with acetone (320 ml), CMH-racemate (40 gr), NaOH (8.56 gr) and 1R, 2S-(-)-Ephedrine hydrochloride (43.16 gr). The mixture was heated to reflux and stirred at reflux for 1 h. The mixture was cooled to 2° C., and after stirring (1 h) at 2° C. the precipitate was filtered. Water (320 ml) was added to the wet solid and the mixture was heated until dissolution. After cooling to RT, HCl-32% (10 ml) was added. The solution was cooled to 2° C., stirred for 1 h, after which the precipitate was filtered. Water (320 ml) was added to the cake and the mixture was stirred at 20° C. for 1 h. The precipitate was filtered, washed with water (20 ml) and dried at 45° C. under 10 mm Hg. (R)-CMH was obtained (12.5 gr), 98.4% optical pure.

Example 11

Preparation of (R)-CMH (All Steps)

1 l flask was charged with acetone (1600 ml), water (40 ml), CMH-racemate (200 gr), and 1R, 2S-(-)-Ephedrine (186.1 gr). The mixture was heated to reflux and stirred at reflux for 1 h. The solution was cooled to 2° C. (during a period of 6 h), and after stirring (10 h) at 2° C. the precipitate was filtered and washed with acetone (400 ml).

Water (800 ml) was added to the wet solid and then HCl-32% (50 ml) was added dropwise to pH 2. The mixture was cooled to 2° C., stirred for 2 h, after which the precipitate was filtered and washed with water (100 ml).

Water (1000 ml) was added to the cake and the mixture was stirred at 25° C. for 1 h. The precipitate was filtered, washed with water (100 ml) and dried at 45° C. under 10 mm Hg. R-CMH was obtained (72 gr), 99.94% optical pure.

Example 12

Preparation of (S)-CMH

The mother liquor residue of example 10, containing (S)-CMH and a residue of (R)-CMH, was dissolved in water and was heated to dissolution. After cooling to RT, HCl-32% (12 ml) was added and mixture was stirred for 30 min at RT. The precipitate, of (R)-CMH was filtered and washed with water (20 ml), while the (S)-CMH remained in the filtrate.

A 0.5 L flask was charged with the later cake of the filtered (R)-CMH, acetone (150 ml), NaOH (4.3 gr) and 1R, 2S-(-)-Ephedrine hydrochloride (21.5 gr). The mixture was stirred at RT for 1 h and the precipitate, of (R)-CMH-ephedrine salt, was filtered. The filtrate containing the remaining (S)-CMH-ephedrine salt, was evaporated to dryness. The residue (44 gr) was dissolved in water (100 ml) and HCl-32% was added until pH=1. The mixture was stirred for 30 min at RT, then the precipitate was filtered, washed with water (20 ml) and dried at 45° C. under 10 mm Hg. (S)-CMH was obtained (11.4 gr), 99.0% optical pure.

What is claimed:

1. A process for the optical resolution of (±)-3-(carbamoyl-methyl)-5-methyl-hexanoic acid (CMH-racemate),

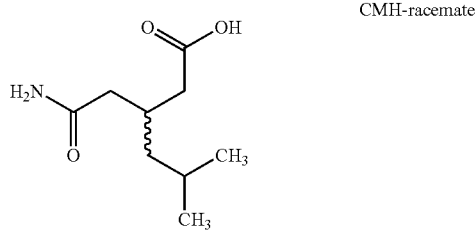

CMH-racemate comprising:
  a) combining CMH-racemate; a solvent selected from the group consisting of $C_3$-$C_6$ ketone, $C_{1-4}$ alcohol, and mixtures thereof; and a chiral resolving reagent of selected from ephedrine, ephedrine salt, norephedrine, and norephedrine salt to obtain a precipitate;

b) isolating the precipitate; and
c) adding to the precipitate a solvent selected from the group consisting of ketone, $C_{1-8}$ alcohol, water and mixtures thereof, and a strong mineral acid;
wherein the precipitate comprises a CMH salt that contains less than about 7% area by HPLC of the (S)—CMH salt and more that about 93% area by HPLC of the corresponding (R)-CMH salt.

2. The process of claim 1, wherein the precipitate comprises a CMH salt that contains less then about 4% area by HPLC of the (S)-CMH salt and more that about 96% area by HPLC of the corresponding (R)-CMH salt.

3. The process of claim 2, wherein the precipitate comprises a CMH salt that contains less then about 0.2% area by HPLC of the (S)-CMH salt and more that about 99.8% area by HPLC of the corresponding (R)-CMH salt.

4. The process of claim 3, wherein the precipitate comprises a CMH salt that contains less then about 0.1% area by HPLC of the (S)-CMH salt and more that about 99.9% area by HPLC of the corresponding (R)-CMH salt.

5. The process of claim 1, wherein the salt in step (a) is a hydrochloride, nitrate or sulfate.

6. The process of claim 5, wherein the salt is a hydrochloride.

7. The process of claim 1, wherein the chiral resolving reagent is ephedrine or ephedrine salt.

8. The process of claim 7, wherein the chiral resolving reagent consisting of an amino alcohol or a salt thereof is 1R,2S-(−)-ephedrine.

9. The process of claim 1, wherein the chiral resolving reagent is a salt of ephedrine or of norephedrine.

10. The process of claim 9, wherein a base is added.

11. The process of claim 10, wherein the base is either an organic base or an inorganic base.

12. The process of claim 11, wherein the organic base is an amine.

13. The process of claim 12, wherein the amine is tertiary or secondary amine.

14. The process of claim 13, wherein the tertiary amine is triethylamine or tributylamine.

15. The process of claim 14, wherein the tertiary amine is triethylamine.

16. The process of claim 13, wherein the secondary amine is diisopropylamine or di-n-propyl amine.

17. The process of claim 11, wherein the inorganic base is an alkali metal hydrogen carbonate, alkali hydroxide or alkali carbonate.

18. The process of claim 17 wherein the alkali hydroxide is either NaOH or KOH.

19. The process of claim 18 wherein the alkali hydroxide is NaOH.

20. The process of claim 17 wherein the alkali carbonate is either $K_2CO_3$ or $Na_2CO_3$.

21. The process of claim 1, wherein the ketone is a $C_3-C_5$ ketone.

22. The process of claim 1, wherein the ketone is either acetone or methyl isobutyl ketone.

23. The process of claim 22, wherein the ketone is acetone.

24. The process of claim 1, wherein the $C_{1-4}$ alcohol is selected from the group consisting of methanol, ethanol, isopropanol, and isobutanol.

25. The process of claim 24, wherein the $C_{1-4}$ alcohol is methanol.

26. The process of claim 1, wherein the strong mineral acid is HCl, HBr, $H_2SO_4$ or $H_3PO_4$.

27. The process of claim 26, wherein the strong mineral acid is HCl.

28. The process of claim 1, wherein after the addition of the acid, a pH of about 0 to about 4 is obtained.

29. The process of claim 28, wherein after the addition of the acid, a pH of about 1 to about 3 is obtained.

30. The process of claim 1, wherein the ketone of step c) is acetone.

31. The process of claim 1, wherein the $C_{1-8}$ alcohol, which is added with the strong mineral acid, is methanol.

32. The process of claim 1, wherein the solvent of step c) is a mixture of water and ketone or water and $C_{1-8}$ alcohol.

33. A process for the optical resolution of (±)-3-(carbamoylmethyl)-5-methyihexanoic acid (CMH-racemate),

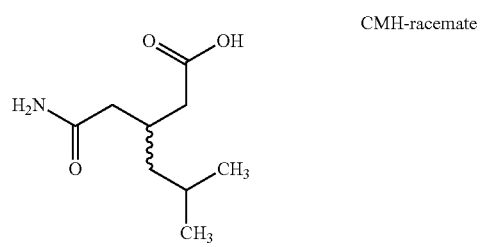

CMH-racemate comprising:
a) combining CMH-racemate, a solvent selected from the group consisting of a $C_3-C_6$ ketone, a $C_{1-4}$ alcohol, and mixtures thereof, and a chiral resolving reagent selected from the group consisting of ephedrine, ephedrine salt, norephedrine and norephedrine salt to obtain a precipitate, wherein the precipitate is of (R)-CMH-ephedrine salt of the following structure:

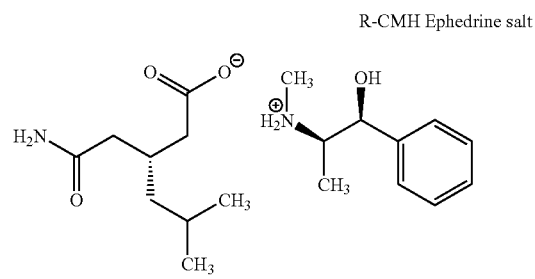

R-CMH Ephedrine salt or of (R)-CMH-norephedrine salt of the following structure:

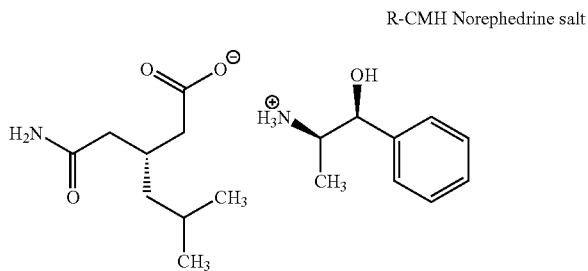

R-CMH Norephedrine salt b) isolating the precipitate; and
c) combining the precipitate with a solvent selected from the group consisting of ketone, $C_{1-8}$ alcohol, water and mixtures thereof, and with a strong mineral acid to obtain a precipitate of (R)-CMH of the following structure

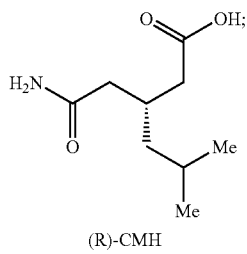
(R)-CMH wherein the precipitated comprises a CMH salt that contains less then about 7% area by HPLC of the (S)-CMH salt and more that about 93% area by HPLC of the corresponding (R)-CMH salt.

34. A process for the optical resolution of (±)-3-(carbamoylmethyl)-5-methyl-hexanoic acid (CMH-racemate),

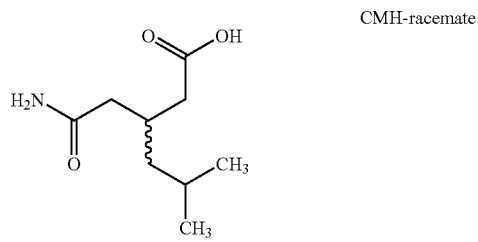
CMH-racemate comprising:
a) combining CMH-racemate, a solvent selected from the group consisting of a $C_3$-$C_6$ ketone, a $C_{1-4}$ alcohol, and mixtures thereof, and 1R, 2S-(−)-ephedrine to obtain a reaction mixture;
b) heating the reaction mixture to a temperature of about 50° C. to about 140° C.;
c) cooling the reaction mixture to a temperature of about 20° C. to about -20° C. to obtain a precipitate, wherein the precipitate is of (R)-CMH-ephedrine salt of the following structure:

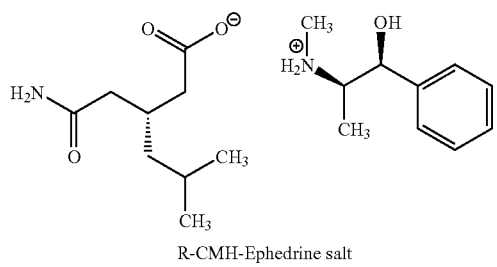
R-CMH-Ephedrine salt d) isolating the precipitate;
e) combining the precipitate with a solvent selected from the group consisting of ketone, $C_{1-8}$ alcohol, water and mixtures thereof, and a strong mineral acid, to obtain a slurry; and
f) cooling the slurry to a temperature of about 10° C. to about 2° C. to obtain a precipitate of (R)-CMH of the following structure:

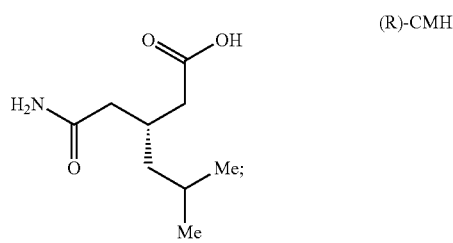
(R)-CMH wherein the precipitated comprises a CMH contains less than about 7% area by HPLC of the (S)-CMH salt and more that about 93% area by HPLC of the corresponding (R)-CMH salt.

35. The process of claim 33, wherein the chiral resolving reagent is ephedrine salt or norephedrine salt.

36. The process of claim 35, wherein the chiral resolving reagent is combined with a base.

37. The process of claim 33, wherein the reaction mixture is heated in step b) to a temperature of about 50° C. to about 100° C.

38. The process of claim 37, wherein the reaction mixture is maintained at a temperature of about 50° C. to about 100° C. for about 0.5 hour to about 5 hours.

39. The process of claim 33, wherein the reaction mixture obtained in step a) is a solution.

40. The process of claim 34, wherein the cooling in step c) is maintained for about an hour to about 24 hours.

41. The process of claim 34, wherein the slurry is cooled to a temperature of about 2° C.

42. The process of claim 34, wherein the slurry is maintained at a temperature of about 2° C. to about ambient temperature.

43. The process of claim 42, wherein the slurry is maintained at a temperature of about 2° C. to about 10° C.

44. The process of claim 42, wherein the slurry is maintained for about 0.5 hours to about 24 hours.

45. The process of claim 33, further comprising recovering the precipitate of (R)-CMH.

* * * * *